United States Patent [19]

Magruder et al.

[11] Patent Number: 5,112,614
[45] Date of Patent: May 12, 1992

[54] IMPLANTABLE DELIVERY DISPENSER

[75] Inventors: Judy A. Magruder, Mt. View; James B. Eckenhoff; Jeremy C. Wright, both of Los Altos, all of Calif.

[73] Assignee: Alza Corporation, Palo Alto, Calif.

[21] Appl. No.: 407,489

[22] Filed: Sep. 14, 1989

[51] Int. Cl.⁵ .................... A61M 37/00; A61K 9/107
[52] U.S. Cl. .................... 424/422; 424/423; 424/424; 424/438; 424/486; 424/488
[58] Field of Search ............... 424/422, 424, 425, 426, 424/428, 486, 498, 502

[56] References Cited

U.S. PATENT DOCUMENTS

| | | | |
|---|---|---|---|
| 2,200,429 | 5/1940 | Perrin et al. | 260/80 |
| 2,386,347 | 10/1945 | Roland, Jr. | 260/86 |
| 2,396,785 | 3/1946 | Hanford | 260/78 |
| 2,399,653 | 5/1946 | Roland, Jr. | 260/86 |
| 2,947,735 | 8/1960 | Bartl | 260/87.3 |
| 3,386,978 | 6/1968 | Salyer | 260/87.3 |
| 3,494,908 | 2/1970 | Hayes | 260/89.1 |
| 3,553,174 | 1/1971 | Hausslein et al. | 260/77.5 |
| 3,845,480 | 10/1974 | Steinberg | 340/236 |
| 3,845,761 | 11/1974 | Zaffaroni | 128/130 |
| 3,845,770 | 11/1974 | Theeuwes et al. | 128/260 |
| 3,896,819 | 7/1975 | Zaffaroni et al. | 128/130 |
| 3,916,899 | 11/1975 | Theeuwes et al. | 128/260 |
| 3,921,632 | 11/1975 | Bardani | 128/217 |
| 3,921,636 | 11/1975 | Zaffaroni | 424/486 |
| 3,996,934 | 12/1976 | Zaffaroni | 424/434 |
| 4,008,864 | 2/1977 | Torphammar et al. | 242/107.4 R |
| 4,063,064 | 12/1977 | Saunders et al. | 219/121 L |
| 4,077,407 | 3/1978 | Theeuwes et al. | 128/260 |
| 4,085,264 | 4/1978 | Seib et al. | 526/47 |
| 4,111,202 | 9/1978 | Theeuwes | 424/473 |
| 4,188,951 | 2/1980 | Higuchi et al. | 128/260 |
| 4,200,098 | 4/1980 | Ayer et al. | 128/260 |
| 4,200,561 | 4/1980 | Chang | 424/81 |
| 4,285,987 | 8/1981 | Ayer et al. | 427/3 |
| 4,451,254 | 5/1984 | Dinius et al. | 604/62 |
| 4,814,182 | 3/1989 | Graham et al. | 424/486 |
| 4,859,470 | 8/1989 | Guittard et al. | 424/464 |
| 4,876,093 | 10/1989 | Theeuwes et al. | 424/469 |

FOREIGN PATENT DOCUMENTS

| | | |
|---|---|---|
| 569927 | 6/1945 | United Kingdom . |
| 582093 | 11/1946 | United Kingdom . |
| 1205764 | 9/1970 | United Kingdom . |
| 1205765 | 9/1970 | United Kingdom . |
| 1205769 | 9/1970 | United Kingdom . |

OTHER PUBLICATIONS

J. Pharm. Sci., vol. 68, No. 7, (1979), pp. 860–862.
Encyclopedia of Polymer Sciences & Technology, vol. 10 (1969), pp. 228–306.
"Plasticization & Plasticizer Processes", Advances in Chemistry Series 48, Amer. Chem. Society (1965), pp. 1–26.
J. Pharm. Sci., vol. 52, No. 12 (1963), pp. 1145–1149.
J. Pharm. Sci., vol. 53, No. 7, (1964), pp. 798–802.
J. Pharm. Sci., vol. 54, No. 10 (1965), pp. 1459–1464.
J. Pharm. Sci., vol. 55, Nos. 8 & 11 (1966), pp. 840–843 & 1224–1239 (II, III & IV).
Encyclopedia of Polymer Science & Technology, vol. 5 (1966), pp. 65–82 and vol. 9 (1968), pp. 794–807 (John Wiley & Sons, Inc.).
Crystalline Olefin Polymers, Part II, (1964), pp. 261–266, Interscience Publishers (John Wiley & Sons, Inc.).

Primary Examiner—Thurman K. Page
Assistant Examiner—Edward J. Webman

[57] ABSTRACT

An implantable dispenser is enclosed comprising a wall surrounding a compartment containing a first composition comprising a beneficial agent, an oil, a cosolvent and a polymer gellant, a second expandable composition, a third boundary maintaining composition between the first and second composition, and an exit port.

19 Claims, 1 Drawing Sheet

IMPLANTABLE DELIVERY DISPENSER

DESCRIPTION OF TECHNICAL FIELD

This invention pertains to both a novel and unique implantable delivery dispenser. More particularly, the invention relates to an improvement in an implantable delivery dispenser comprising a pharmaceutically acceptable vehicle for storing and for delivering a beneficial agent at a substantially controlled rate to an animal environment of use.

DESCRIPTION OF BACKGROUND ART

Implants for delivering a beneficial agent such as a drug are known to the prior art in *Remington's Pharmaceutical Sciences*, 4th Ed., pp 1714-17, (1970) published by the Mack Publishing Company. Generally, the implants known to the prior art comprise a nonerodible matrix, an erodible matrix, or a capsule. More specifically, the nonerodible matrix implant comprises a drug dispersed in a polymer. A drug is released, when the matrix implant is in an aqueous biological environment, by diffusing from the implant, or the drug is leached from the implant. This implant initially releases a drug at a constant rate followed by a rate that declines over time. An erodible implant generally comprises a drug dispersed in a polymer that dissolves or erodes in body fluids. As this implant loses its physical and chemical integrity, it exhibits an accompanying decrease in the rate of drug delivery over time. Capsule implants are made with an erodible or a nonerodible wall, and in the former manufacture it releases the drug instantly, and in the latter it releases the drug in a declining rate over time.

In view of the above presentation, it will be self-evident to those versed in the implant art that a pressing need exists for an implant which is biocompatible and releases a beneficial agent at a constant and predetermined rate over time. The need exists for an implant manufactured as an implantable dispenser useful for delivering, for example, steroids, peptides and other agents which would benefit a host therapeutically from long duration implantation. It will be appreciated that if a novel implantable delivery dispenser is made available that possesses the kinetic ability to deliver a beneficial agent at a controlled rate over time, such an implantable delivery dispenser would have a practical application in the fields of human and veterinary medicine.

DISCLOSURE OF OBJECTS OF THE INVENTION

Accordingly, in view of the above presentation it is an immediate object of this invention to provide an implantable delivery dispenser for administering a beneficial agent, and which implantable delivery dispenser overcomes the limitations associated with the prior art.

Another object of the invention is to provide an implantable delivery dispenser that is biocompatible and releases a beneficial agent at a predetermined constant rate over time.

Another object of the invention is to provide an implantable delivery system for delivering a beneficial agent to a human or to a veterinary host with the implantable dispenser releasing the beneficial agent at a rate controlled by the dispenser and, when the release is terminated abruptly, the implantable dispenser leaves a minimal agent residue in the dispenser and in the host.

Another object of the invention is to provide an implantable dispenser that can be manufactured by standard manufacturing techniques for delivering in vivo a beneficial agent, such as a drug, that is difficult to deliver and now can be delivered by the implantable dispenser of this invention in therapeutically effective amounts over time.

Another object of the invention is to provide an implantable delivery dispenser that is implantable using simple injection techniques and does not require extensive surgery for its placement in a biological tissue.

Another object of the invention is to provide an implantable dispenser comprising a pharmaceutically acceptable vehicle, which vehicle comprises at least one of a drug and an oil; a drug, an oil and a cosolvent; and a drug, an oil, a cosolvent and a polymer that imparts gel properties to the oil and cosolvent thereby providing a vehicle that effects a constant drug delivery pattern over a prolonged period of time.

Another object of the invention is to provide an implantable dispenser comprising a pharmaceutically acceptable vehicle comprising biocompatible oils and oil gellants.

Another object of the invention is to provide an implant dispenser that can be placed under the skin, or in the muscle of a ruminant animal, for releasing an effective amount of a beneficial agent for causing the animal to gain weight at a greater than normal rate.

Another object of the invention is to provide an implant dispenser for synchronizing estrus in a female animal.

Another object of the invention is to provide an implant dispenser for dispensing a steroid for estrus suppression with an accompanying weight gain in the animal.

Another object of the invention is to provide an implant dispenser for delivering a drug to livestock, including cattle, swine and pigs, over time, and wherein the implant dispenser is shaped, sized and adapted for implanting in the muscle tissues of an animal for delivering the drug over a broad range of dosage delivery rates according to predetermined time release patterns.

Another object of the invention is to provide an implant that is compact in size and shaped for easy placement within the lumen of a trocar, or within similar implanting instruments that are limited in dimensions and, consequently, reduce trauma and discomfort to a receiving animal.

Another object of the invention is to provide an implant shaped at one of its ends in a conical or spherical shape for reducing the force necessary to push the implant into an implant receiving site, thereby reducing the incidence of tissue damage and the incidence of damage to the implant, thereby enhancing the process of implantation.

Other objects, features and advantages of the invention will be more apparent to those versed in the dispensing art from the following detailed specification taken in conjunction with the accompanying claims.

BRIEF DISCLOSURE OF THE DRAWING FIGURES

In the drawing figures, which are not drawn to scale, but are set forth to illustrate various embodiments of the invention, the drawing figures are as follows.

In the drawing figures and in the specification, like parts in related drawings are identified by like numbers. The terms appearing earlier in the specification and in the description of the drawings, as well as embodiments thereof, are further detailed elsewhere in the disclosure.

DETAILED DISCLOSURE OF DRAWING FIGURES

Figure 1:
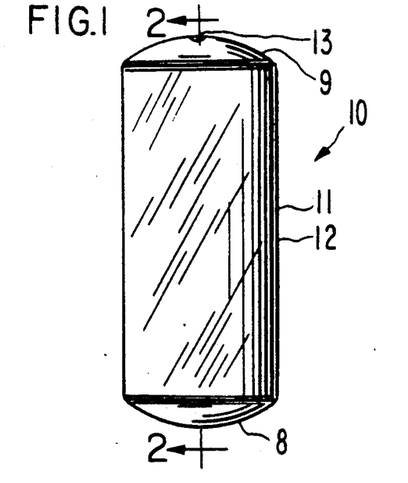
FIG. 1 is a view of an implantable delivery dispenser provided by the invention for delivering a beneficial agent to an animal.

Turning now to the drawing figures in detail, which drawing figures are examples of various implantable delivery dispensers provided by the invention, and which examples are not to be construed as limiting the invention, one example of an implantable delivery dispenser is seen in FIG. 1 and identified by the number 10. In FIG. 1, the implantable dispenser comprises a body 11, which body 11 comprises a wall 12. Wall 12 surrounds an internal compartment, not seen in FIG. 1. Implant dispenser 10 comprises at least one passageway 13 for delivering a beneficial agent formulation from implant dispenser 10. In FIG. 1, in the embodiment illustrated, implant dispenser 10 comprises a domed-shaped lead end 9 and a similar domed-shaped rear end 8 for aiding in placing implant dispenser 10 in an animal host. In an optional embodiment not seen, implant dispenser 10 can be manufactured with flat ends 8 and 9, or other shaped ends.

Implant dispenser 10, as seen in drawing FIG. 1, can be used for administering a beneficial agent including a drug in many applications. For example, implant dispenser 10 can be used for (1) administering a beneficial agent directly to body tissues, when an orally administered agent does not show sufficient activity in the gastrointestinal tract, and implant 16 exhibits unexpected results when administering the beneficial agent directly to tissues, for (2) administering a beneficial agent over a prolonged period of time up to 210 days or longer, for (3) administering at a substantially constant rate a beneficial agent for better control of beneficial agent administration, for (4) administering a beneficial agent from the implantable dispenser that is implanted using simple injection techniques that do not require surgery, for (5) administering a beneficial agent by an implant dispenser that exhibits abrupt termination of agent release obviating the need to remove the dispenser, for (6) administering less beneficial agent to achieve improved results such as, weight gain, estrus suppression, or the like, for (7) administering different beneficial agents for producing different results such as, unexpectedly superior weight gain in animals, for estrus suppression in heifers accompanied by weight gain, and the like, for (8) implanting an implantable dispenser that does not require protective measure, and for (9) administering a beneficial agent from the implanted dispenser when the beneficial agent is sensitive to acid and to alkaline environments.

Figure 2:
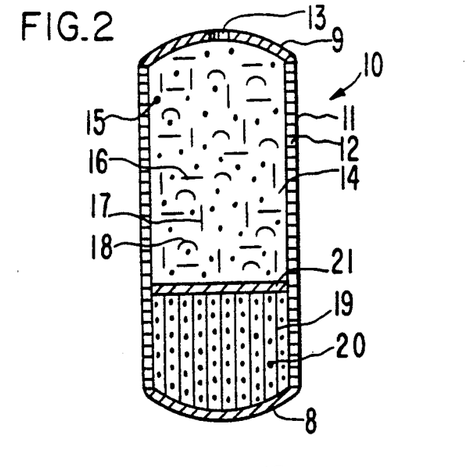
FIG. 2 is an opened view of the implantable dispenser of FIG. 1 through 2—2 of FIG. 1, for illustrating one structural embodiment of the implant provided by the invention.

Drawing FIG. 2 depicts implant 10 in opened view through 2—2 of implant dispenser 10 as seen in FIG. 1. Implant dispenser 10 of FIG. 2 comprises body 11, wall 12, lead end 9, trailing end 8 and exit passageway 13. Wall 12 surrounds and defines an internal compartment 14. Wall 12, in a presently preferred embodiment, comprises a wall-forming composition that is permeable to the passage of aqueous and biological fluids and it is substantially impermeable to the passage of a beneficial agent 15 and other ingredients contained in implant dispenser 10. Wall 12, in another embodiment, comprises at least in part a wall-forming composition permeable to the passage of aqueous-type fluids. Wall 12 is permeable in total or in part for making available external aqueous-type fluid to an expandable composition housed in compartment 14. Lead end 9 and trailing end 8 can be made continuous with wall 12 or, in another manufacture lead end 9 and trailing end 8 can be made separately of the same or of a different composition that are fixed or releasably joined to wall 12. In one presently preferred manufacture, trailing end 8 comprises a composition permeable to the passage of an exterior fluid for making it available to an expandable driving composition 19 in compartment 14. Wall 12, and ends 9 and 8, optionally comprise a wall-forming composition which is a means for increasing or for decreasing the permeability of wall 12 and ends 9 and 8 to the passage of an external fluid. Wall 12 optionally comprises a non-toxic plasticizer that imparts flexibility and workability to wall 12. Wall 12, ends 9 and 8 are essentially non-toxic, and they maintain their physical and chemical integrity during the beneficial agent delivery period.

Internal compartment 14 of implant 10 comprises a beneficial agent formulation. The beneficial agent formulation comprises (a) a beneficially active agent 15 identified by dots, (b) a pharmaceutically acceptable oil 16 identified by horizontal dashes, (c) a pharmaceutically acceptable polymer 17 identified by vertical lines, which polymer is a gellant for oil 16, and (d) a cosolvent 18 identified by half circles. The three components, oil 16, cosolvent 18 and polymer 17 are used separately or in combination to provide a pharmaceutically acceptable carrier or vehicle for beneficial agent 15. The oil and the cosolvent 18 are used by the present invention to enhance significantly the solubility and a high concentration of beneficial agent 15 in a pharmaceutically acceptable non-aqueous vehicle. The cosolvent also is a permeation enhancer that aids in the absorption and penetration of beneficial agent 15 into a biological tissue. As the gellant polymer imparts dispensable properties to the pharmaceutical vehicle it increases the solubility of a beneficial agent that exhibits a low solubility in an aqueous media; it aids in filling and manufacturing the implant; it assists in increasing the concentration of a beneficial agent in implant 10; and it acts as gellant so vehicle has a high viscosity.

Implant 10 as seen in drawing FIG. 2, comprises a layer 21 positioned between the beneficial agent composition 15 and a push driving composition 19. Layer 21 comprises a composition that is substantially impermeable to the passage of fluids, oils and agents, and it serves to substantially prevent the passage of beneficial agent 15 into push composition 19. Layer 21 insures that the push force generated by composition 19 is applied against beneficial agent 15. Push composition 19 comprises a hydrogel that imbibes, absorbs and expands when contacted by fluid that enters the implant thereby pushing against composition 15 and displacing it from implant 10. In another manufacture, push composition 19 comprises an osmagent 20 that imbibes fluid and forms a solution that increases in volume which pushes composition 15 from implant 10. Also, in another optional embodiment, push composition 19 comprises a hydrogel and an osmagent 20 that act together for displacing beneficial agent 15 from implant 10.

Figure 3:
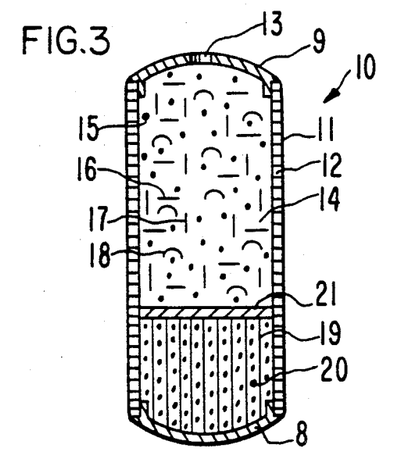
FIG. 3 is an opened view of the implant dispenser which illustrates another embodiment of the dispenser adapted for delivering a steroid, peptide or other drug to livestock.

Drawing FIG. 3 illustrates an opened view of another embodiment of the implantable dispenser 10. In drawing FIG. 3, implant 10 comprises body 11, wall 12, exit passageway 13, compartment 14, beneficial agent 15, oil 16, gellant 17, cosolvent 18, push composition 19, osmagent 20, and fluid impervious push transferring layer 21. In drawing FIG. 3, implant 10 comprises a lead or head cap 9 that closes lead end 9 of wall 12. Implant 10 comprises an end cap 8 adapted to close the end of wall 12. Caps 9 and 8 can be made by injection molding, pressing, or the like into a shape that engages and closes the lead and end of wall 12. End cap 8, in a presently preferred manufacture, is permeable to the passage of water and biological fluids.

Figure 4:
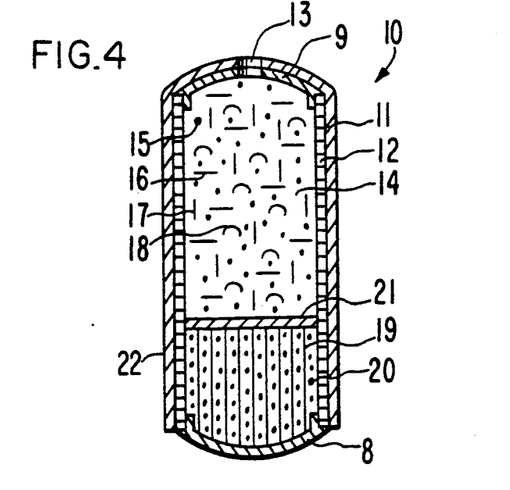
FIG. 4 is an opened view of the implant dispenser illustrating the dispenser comprising an exterior coat.
Figure 5:
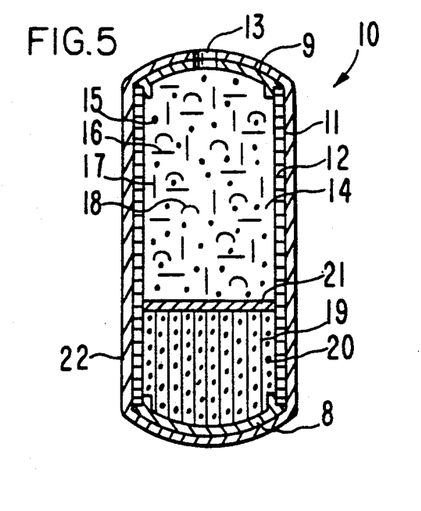
FIG. 5 is an opened view of the implant dispenser illustrating the dispenser comprising an exterior coat around the entire exterior surface of the dispenser; and, FIG. 6 is an opened view of the implant dispenser provided by the invention, which opened view depicts the dispenser comprising the internal components in a bilayered arrangement at the beginning of the delivery period.

Drawing FIG. 4 illustrates another implant 10 provided by the invention. In drawing FIG. 4, implant 10 comprises lead end 9, rear end 8, body 11, wall 12, exit port 13, compartment 14, beneficial agent 15, oil 16, gellant polymer 17, cosolvent 18, push transmitting layer 21, push composition 19 and osmagent 20. In drawing FIG. 4, implant 10 comprises an outer coat 22 that covers a major area of wall 12, particularly the wall area that surrounds the beneficial composition 15. Coat 22, in the embodiment illustrated, is in contact with the complete exterior surface of wall 12, except for rear end 8, which rear end 8 permits the passage of aqueous fluids into push composition 19. Accompanying FIG. 5, in another embodiment, illustrates dispenser 10 wherein coat 22 surrounds the complete exterior surface of wall 12, with the proviso that coat 22 is semipermeable in at least the area adjacent to end cap 8 and allows for the passage of exterior fluid into end cap 8. In another manufacture not shown, coat 22 is in contact with the exterior surface of wall 12 that corresponds to the interior area occupied by the beneficial agent composition. In this embodiment, coat 22 comprises a composition impermeable to the passage of an exterior aqueous fluid, also in this embodiment the exterior surface of wall 12 that corresponds to the internal area occupied by push composition 19 can be (a) coated with a coating composition permeable to fluid for making fluid available to wall 12, or the exterior surface corresponding to the push member 19 can (b) remain free of the exterior coat 22, thereby making fluid available to the exterior surface of wall 12.

Figure 6:
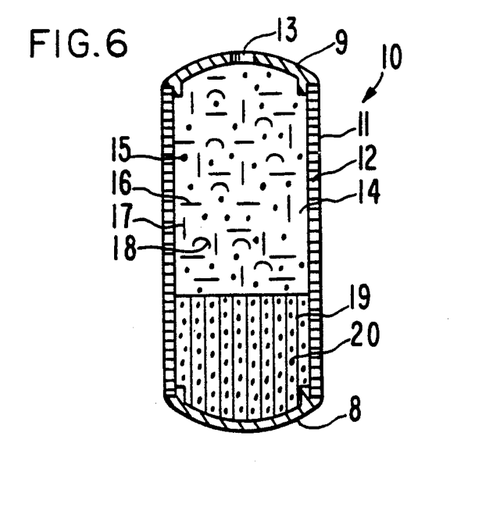

Drawing FIG. 6 illustrates another implant dispenser 10 and is seen in opened section. In drawing FIG. 6, implant dispenser 10 is manufactured as in drawing FIGS. 1 to 4, except for the absence of layer 21. In drawing FIG. 6, implant dispenser 10 is manufactured without layer 21, when beneficial agent composition 15 and push composition 19 independently comprise materials that are incompatible and exhibit a minimum tendency to mix with each other.

The implant dispenser 10 of FIGS. 1 through 6 can be manufactured for delivering numerous beneficial agents, including drugs, at a controlled rate to a biological environment, such as a warm-blooded animal, including humans and livestock. The implant provides for high loading of a beneficial agent, and for its delivery in therapeutically effective amounts over time. FIGS. 1 through 6 are illustrative of various implants that can be made according to this invention. In one presently preferred manufacture, the implant is made having a cylinder shape with hemisphere ends. In another preferred manufacture the implant is made with conical ends for ease of implantation into a subcutaneous space. The implant, in one manufacture for example, can comprise a cylindrical implant having a length of from about 0.5 cm to 8 cm. Preferably the implant is from 2 cm to 4 cm in length, and in a more presently preferred embodiment from about 2.5 cm to 3.5 cm in length. The diameter of the implant is about 2 mm to 20 mm, with a more presently preferred diameter of about 3 mm to 5 mm. The thickness of the coating 22 applied to the exterior surface of the implant 10 is generally 0.01 mm to 8 mm and, in a presently preferred embodiment it comprises thicknesses of about 0.05 mm to 0.5 mm, 0.25 mm to 2 mm, and the like. It is additionally to be understood, the implants described herein are not to be limiting, as the implant can take a wide variety of shapes, sizes and forms adapted for delivering beneficial agents to an environment of use. For example, the implants can be made for delivering a beneficial agent to buccal, muscle, subcutaneous and like tissue receiving areas.

The implants can be implanted into implant receiving tissue by using an implanter. Generally, an implanter comprises a tubular member with a central longitudinal axial bore, a pointed elongated annular concavely bevelled implanting end and an implant charging end. The implanting and the charging ends communicate through the bore. A plunger, adapted to be removably inserted in the bore, is designed for slidable movement therein for applying the necessary force for implanting an implant. Implanters for introducing a therapeutic implant into the body of an animal for providing uniform release of a drug over a long period of time are known in U.S. Pat. Nos. 3,921,632 and 4,451,254, and the documents cited therein.

DISCLOSURE OF MODES OF PERFORMING THE INVENTION

In accordance with the practice of this invention it now has been discovered that implant dispenser 10 of FIGS. 1 to 6 can be made with a wall 12 that surrounds compartment 14. Wall 12 comprises materials that do not adversely affect the beneficial agent, the pharmaceutically acceptable oil, the pharmaceutically acceptable polymer, the expandable driving member, the cosolvent and other ingredients in compartment 14, a host, and the like. Wall 12, in one preferred manufacture comprises a semipermeable composition that controls fluid flux into implant 10. In another preferred embodiment wall 12 comprises at least in part a semipermeable composition that controls fluid flux, with the remaining part substantially impermeable to the passage of fluid. Wall 12 in another embodiment comprises a semipermeable composition and means for aiding in regulating the fluid flux of wall 12. In an optional embodiment, wall 12 comprises a non-toxic plasticizer for imparting manufacturing properties to wall 12.

The semipermeable composition of wall 12 is permeable to the passage of external fluids such as water and biological fluids, and it is substantially impermeable to the passage of beneficial agents, osmagents, osmopolymers, and the like. Typical semipermeable materials for forming wall 12 are, in one presently preferred embodiment, a member selected from the group consisting of a cellulose ester, a cellulose ether, or a cellulose ester-ether. The cellulose polymers have a degree of substitution, D.S., on the anhydroglucose unit from greater than 0 up to 3 inclusive. By, "degree of substitution," we mean the average number of hydroxyl groups originally present on the anhydroglucose unit comprising the cellulose polymers that are replaced by a substituting group. Representative materials include, but are not limited to, a member selected from the group consisting of a cellulose acylate; cellulose diacylate; cellulose triacylate; cellulose acetate; cellulose diacetate; cellulose triacetate; mono-, di-, and tricellulose alkanylates; mono-, di-, and tricellulose aroylates, and the like. Exemplary cellulosic polymers include cellulose acetate having a D.S. up to 1 and an acetyl content up to 21%; cellulose acetate having an acetyl content of 32% to 39.8%; cellulose acetate having a D.S. of 1 to 2 and an acetyl content of 21% to 35%; cellulose acetate having a D.S. of 2 to 3 and an acetyl content of 35% to 44.8%, and the like. L. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8, an acetyl content of 13% to 15% and a butyryl content of 34% to 39%; cellulose acetate butyrate having an acetyl content of 2 to 29%, a butyryl content of 17% to 53% and a hydroxyl content of 0.5% to 1.7%; cellulose acetate butyrate having a D.S. of 1.8, an acetyl content of 4% and a butyryl content of 51%; cellulose triacylate having a D.S. of 2.9 to 3 such as cellulose trivalerate, cellulose trilaurate, cellulose tripalmitate, cellulose trisuccinate, and cellulose trioctanoate; cellulose diacylate having a D.S. of 2.2 to 2.6 such as cellulose disuccinate, cellulose dipalmitate, cellulose dioctanoate, and cellulose dipentate; coesters of cellulose such as cellulose acetate butyrate and cellulose acetate propionate, and the like. The amount of a semipermeable cellulosic polymer presently preferred in wall 12 is about 35 to 100 weight percent (wt %).

Wall 12, in another manufacture, comprises a composition comprising a cellulose polymer and an acrylate polymer. The cellulosic polymer comprises at least one cellulosic polymer selected from the above disclosed cellulosic polymers. The acrylate polymer comprises at least one member selected from the group consisting of polymethacrylate; polymethylmethacrylate; polyhydroxyethylmethacrylate; polysulfoxymethylethylmethacrylate; poly(dimethylaminoethylmethacrylate); poly(hydroxypropylmethacrylate); polyacrylates comprising a monoester of acrylic or methacrylic acid with a bifunctional alcohol comprising an esterfiable hydroxyl group and a hydrophilic functional group, poly(ethylthio)ethylmethacrylate, poly(ethylsulphinyl)ethylmethacrylate, and the like. Wall 12, in this embodiment, comprises from 15% to 80% of a cellulose polymer, from 15% to 80% of an acrylate polymer, and from 0% to 35% of a plasticizer, with the amount of all wall-forming ingredients equal to 100 wt %. The polymers disclosed herein are known to the prior art in *Handbook of Common Polymers*, by Scott and Roff, published by CRC Press, Cleveland, OH; in U.S. Pat. Nos. 3,553,174 and 4,085,264; in G.B. Pat. Nos. 1,205,764; 1,205,765 and 1,205,769; and in *J. Pharm. Sci.*, Vol. 68, No. 7, pp 860-62, (1979).

Wall 12 optionally comprises a non-toxic plasticizer. Representative plasticizers for forming wall 12 comprise plasticizers that lower the temperature of the second-order phase transition of wall 12, or the elastic modulus of wall 12, also, plasticizers that increase the workability of wall 12 and its flexibility. Plasticizers operable for the present purchase comprise straight chain and branched plasticizers, cyclic plasticizers, acrylic plasticizers, and heterocyclic plasticizers. Representative plasticizers comprise a member selected from the group consisting of phthalate, phosphate, citrate, adipate, tartrate, sebacate, succinate, glycolate, glycerolate, benzoate, myristate, sulfonamide, and halogenated plasticizers.

Representative specific plasticizers comprise dialkyl phthalate, dicycloalkyl phthalate, diaryl phthalate, dimethyl phthalate, dipropyl phthalate, di(2-ethylhexyl) phthalate, diisopropyl phthalate; alkyl phosphate, aryl phosphate, tributyl phosphate; trioctyl phosphate, tricresyl phosphate, and triphenyl phosphate, alkyl citrate, citrate esters, tributyl citrate, trimethyl citrate, triethyl citrate, and acetyl triethyl citrate; alkyl adipates such as dioctyl adipate, diethyl adipate and di(2-methoxyethyl)adipate; dialkyl tartrates such as diethyl tartrate, and butyl tartrate; alkyl sebacates such as diethyl sebacate, dipropyl sebacate and dinonyl sebacate; alkyl succinates such as diethyl succinate and dimethyl succinate; alkylglycolates; alkyl glycerolates; glycol esters; glycerol esters such as glycerol diacetate, glycerol triacetate, glycerol monolactate diacetate, methyl phthalyl ethyl glycolate, and the like.

Plasticizers can be selected for blending with the wall forming materials by selecting plasticizers that have a high degree of solvent power for the materials; are compatible with the materials over both the processing and use temperature range; exhibit permanence as seen by its strong tendency to remain in the plasticized wall, both in storage and in the biological environment of use; imparts flexibility to the material, and are non-toxic to animals, mammals, humans, avians, fishes and reptiles. Procedures for selecting a plasticizer having the described characteristics are disclosed in the *Encyclopedia of Polymer Sciences and Technology*, Vol. 10, pp 228-306, (1969), published by John Wiley & Sons, Inc. Also, a detailed description pertaining to the measurement of plasticizer properties including solvent parameters and compatibility, such as the Hildebrand solubility parameter, the Flory-Huggins interaction parameter, and the cohesive-energy density, (CED), parameters are disclosed in "Plasticization and Plasticizer Processes," *Advances in Chemistry*, Series 48, Chapt. 1, pp 1-26, (1965), published by the American Chemical Society, and in U.S. Pat. No. 4,077,407.

The fluid flux through a wall polymeric composition can be measured by techniques known to the art. One technique that has been found to be eminently well suited to the art is to cast or hot press a film of the material to a thickness in the range of 0.0254mm to 1.524 mm. The film is used as a barrier between a fluid source and a container initially free of fluid. Then, by measuring the volume of fluid that passed through a film of known area and thickness, the flux is easily ascertained by standard techniques known to the art as recorded in *J. Pharm. Sci.*, Vol. 52, No. 12, (1963) pp 1145-49 and ibid.. Vol. 53, No. 7, (1964) pp 798-802; ibid. Vol. 54, No. 10, (1965) pp 1459-64; ibid.. Vol. 55, No. 8, (1966) pp 840-43 and Vol. 55, No. 11, (1966) pp 1224-39 (II, III, IV); *Encyl. Polymer Sci. Technol.*, Vol.

5, (1966) pp 65-82 and ibid. Vol. 9, (1968) pp 794-807, and the references cited therein; in U.S. Pat. Nos. 3,845,480; 3,845,761 and 3,896,819. Walls that exhibit a fluid permeability of $10^{-6}$ to $10^{-1}$ (cc.mil/cm$^2$. hr atm) can be used for the purpose of this invention. The polymers are known to the art in the *Handbook of Common Polymers*, by J. R. Scott and W. J. Roff, (1971), published by CRC Press, Cleveland, Ohio.

Coat 22, in the manufacture where it is in contact with the exterior surface of wall 12, covers an area essentially equal to the area occupied by the beneficial agent composition in the compartment and it comprises, in this manufacture, a polymeric composition that substantially restricts or totally prevents the passage of an exterior fluid present in the environment from entering compartment 14. Polymeric compositions useful for forming coat 22 comprise olefin polymers, vinyl polymers, addition polymers, condensation polymers, coactivation polymers, coordination polymers and rubber polymers. Representative polymers include fluid restricting polyethylene, polytetrafluroethylene, polycarbonate, polystyrene, polyamide, polyflormaldehyde, polymelamine formaldehyde, polysulfone, styrene-butadiene rubber, fluid impermeable polyurethane, high density polyisobutylene, high density polypropylene, polyvinyl chloride, and the like. Coat 22 in a presently preferred manufacture is a coat-forming composition comprising cellulose acetate butyrate, polymethyl methacrylate and tributyl citrate; cellulose acetate butyrate, polymethyl methacrylate and dioctyl adipate; cellulose acetate propionate, polymethyl methacrylate and trioctyl phosphate; and the like. Coat 22 can be applied using organic solvents, which solvents are vacuum stripped from the coat to leave a dry coat. The polymers can be used additionally for forming end cap 9 of implant 10. The permeability of water through a polymer used for manufacturing coat 22, which is a fluid barrier, can be measured by following the techniques disclosed in *Handbook of Common Polymers*, by J. R. Scott and W. J. Roff, Section 64, (1971) published by CRC Press, Cleveland, Ohio.

The pharmaceutically acceptable oils used for formulating the carrier comprise naturally occurring and synthetic oils. The oils comprise a member selected from the group consisting essentially of organic and inorganic oils such as animal, fruit, marine, mineral, nut, plant, sylvan, and vegetable oils. Examples of specific oils comprises a member selected from the group consisting of herring, whale, babasau, almond, peanut, sesame, castor, cottonseed, olive, palm, rapseed, corn, soybean, eucalyptus, and tung oil. In another embodiment, the oil comprises a silicone fluid. The silicone fluids are commercially available in a range of viscosities from 1 to 100,000 centistokes, or higher. Representative silicone fluids comprise a member selected from the group consisting of dimethylsilicone fluid, methylphenylsiloxylsilicone fluid, diphenylsiloxylsilicone fluid, methylvinylsiloxylsilicone fluid, methyltrifluropropylsilicone fluid, polydimethylsiloxane fluid, polydiethylsiloxane, polymethylisopropylsiloxane, and the like. The amount of pharmaceutically acceptable fluid present in compartment 14 of implant 10 is about 35 to 90 wt %, and more preferably about 40 to 70 wt %.

The pharmaceutically acceptable cosolvent that homogeneously blends with the oil for formulating the pharmaceutically acceptable vehicle comprise a member selected from the group consisting of esters of saturated monocarboxylic acids, saturated dicarboxylic acids, and unsaturated aliphatic acid wherein the ester of the acid comprises an alkyl group of 1 to 20 carbons or an aryl of 6 carbon atoms substituted with an alkyl group of 1 to 6 carbons. Representative cosolvents comprise a member selected from the group consisting of butyl stearate, stearyl stearate, propyl stearate, isopropyl stearate, 2-ethylhexyl stearate, myristyl stearate, decyl stearate, benzyl stearate, butyl palmitate, cetyl palmitate, 2-ethylhexyl palmitate, isopropyl palmitate, butyl laurate, isopropyl laurate, hexyl laurate, cetyl laurate, isopropyl myristate, butyl myristate, myristyl myristate, lauryl myristate, isoamyl myristate, decyl oleate, di-isopropyl adipate, di-2-ethylhexyl adipate, di-n-butyl sebacate, di-2-ethylhexyl sebacate, di-isopropyl sebacate, isopropyl linoleate, cetyl lactate, lauryl lactate, myristyl lactate, decyl oleate, isodecyl oleate, and the like. The concentration of cosolvent when used in implant dispenser 10 is from 0 to 40 wt %, more frequently from 5 to 35 wt %.

The pharmaceutically acceptable polymer 17 that imparts gel properties to the pharmaceutically acceptable vehicle for substantially keeping a beneficial agent 15 homogeneously or heterogeneously blended or suspended in the pharmaceutical oil or cosolvent comprises a member selected from the group consisting of olefin polymers, vinyl polymers, condensation polymers, addition polymers, cellulosic polymers, saccharide polymers, organo-silicon polymers, and the like. In one presently preferred embodiment, the pharmaceutically acceptable polymer 17 comprises an ethylene-vinyl ester copolymer, such as ethylene-vinyl formate copolymer, ethylenevinyl acetate copolymer, ethylene-vinyl hexanoate copolymer, ethylene-vinyl propionate copolymer, ethylene-vinyl pentanoate copolymer, ethylene-vinyl isopropylate copolymer, ethylene-vinyl diacetate copolymer, ethylene-vinyl tertbutylacetate copolymer, ethylene-vinyl phenylacetate copolymer, ethylene-vinyl benzoate copolymer, and the like. In its broadest aspect, the present invention contemplates the use of ethylene-vinyl ester copolymers comprising a vinyl ester content of about 4% to 80%, a melt index of about 0.1 to 1000 grams per ten minutes, and a density of 0.120 to 1.25. Also, a portion of the acyloxy groups of the copolymer can be hydrolyzed to alcohol groups. The percentage of units hydrolyzed to vinyl alcohol units is about 10% to 60%. The pharmaceutically acceptable polymers can be in the implant in pharmaceutically acceptable forms such as solid, crystalline, microcrystalline, particle, granule, powder, and the like. The amount of pharmaceutically acceptable polymer in the implant generally is about 0.5 to 40 wt %. The polymers are commercially available. Exemplary techniques for their preparations are described in U.S. Pat. Nos. 2,200,429; 2,396,785; 2,947,735, and 4,188,951; in British Pat. Nos. 569,927 and 582,093; and in *Crystalline Olefin Polymers*, Part II, Editors Raff and Doak, (1964) pp 261–66, published by Interscience Publishers, NY; and, exemplary hydrolysis procedures are set forth in U.S. Pat. Nos. 2,386,347; 2,399,653; 3,386,978, and 3,494,908.

The beneficial agent present in the implant 10 comprises beneficial drugs for producing an intended, beneficial effect. For example, the beneficial agent that can be administered by the implant dispenser comprise drugs that act on synaptic and neuroeffector sites, drugs that act on the central nervous system, autocoids, antiinflammatory, analgesic, antipyretic, antibiotics, germicides, and the like. In a more presently preferred embodiment the beneficial agent comprises a steroid that effectively suppresses estrus, can be used for producing a weight gain in an animal, especially heifers, and for synchronizing estrus. Beneficial steroids that can be used for producing these results in animals comprise dromostanolone, dromostanolone propionate, chlormadinone, chlormadinone acetate, dimethisterone, ethisterone, hydroxyprogesterone, norgestomet (17-alpha-acetoxy-11-beta-methyl-19-nor-preg-4-ene,3,20-dione) and other norsteroids such as norethindrone, norgesterone, norethylodrel, norgestrel, noregestrienone, and norgestoniel; melengestrol acetate, estradiol, 17α-acetoxy-11β-methyl-19-norpregn-4-ene-3,20-dione, 3(3-oxo-11β,13β-dialkyl-17β-hydroxygon-4-en-17α-yl)-propionic acidlactone, 3-(3-oxo-11βmethyl-17β-hydroxyestr-4-en-17α-yl)-propionic acid lactone, 11,13β-dialkyl-17 lower alkyl-17 lower alkyl-gon-4-en-3 one, 19-norpregn-4-ene-3,20-dione, and the like.

In another presently preferred embodiment the beneficial agent present in the implant comprises a pharmacologically active polypeptide. Representative polypeptides comprise oxytocin, vasopressin, adrenocorticotropic hormone, epidermal growth factor, prolactin, luliberin, luteinizing hormone releasing factor, growth hormone, growth hormone releasing factor, insulin, somatostatin, glucagon, interferon, gastrin, tetragastrin, pentagastrin, urogestrone, secretin, calcitonin, enkephalins, endorphins, angiotensins, renin, bradykinin, bacitracins, polymyxins, colistins, tyrocidine, gramicidins, synthetic analogues, modifications and pharmaceutically-active fragments of polypeptides, monoclonal antibodies, soluble vaccines, somatropin, somatotropin, cosyntropin, gonadotropins, chorionic gonadotropin, thyrotropin releasing hormone, thyroid stimulating hormone, pancreozymin, enkephalins, and the like. The drugs and their dosage unit amounts are known to the prior art in *The Pharmacological Basis of Therapeutics*, by Gilman, Goodman, Rall and Murad, 7th Ed., (1985), published by MacMillan Publishing Co., NY; and in *Pharmaceutical Sciences*, Remington, 17th Ed., (1985), published by Mack Publishing Co., Easton, Pa. Generally, the implant will comprise from 0.01% to 40 wt % of a beneficial agent.

The phrase, "exit means 13," as used herein, comprises means and methods suitable for the metered release of the beneficial agent from compartment 14 of implantable system 10. The exit means 13 includes at least one passageway, orifice, or the like, through wall 12 for communicating with compartment 14. The expression, "at least one passageway," includes aperture, orifice, bore, pore, porous element through which the agent can migrate; hollow fiber, capillary tube, porous overlay, porous insert, and the like. The expression also includes material that erodes or is leached from the wall in the fluid environment of use to produce at least one passageway in dosage form implant 10. Representative material suitable for forming at least one passageway, or a multiplicity of passageways, include an erodible poly(glycolic) acid or poly(lactic) acid member in the wall; a gelatinous filament; poly(vinyl alcohol); leachable materials such as fluid removable pore forming polysaccharides, salts, or oxides, and the like. The expression includes structural characteristics that concentrate stress at a precise point in the wall so that only a small amount of force will induce breakage in the wall, yielding a passageway through the wall from compartment 14 to the outside of the implant 10. A passageway or a plurality of passageways can be formed by leaching a material such as sorbitol, lactose and like water-soluble solids from the wall. The passageway can have any shape such as round, triangular, square, elliptical, and the like, for assisting in the metered release of beneficial agent from dosage form implant 10. Dosage form implant 10 can be constructed with one passageway or more than one passageway in spaced apart relations on one or more than one surface of a dosage form. Passageways and equipment for forming passageways are disclosed in U.S. Pat. Nos. 3,845,770; 3,916,899; 4,063,064 and 4,008,864. Passageways formed by leaching are disclosed in U.S. Pat. Nos. 4,200,098 and 4,285,987.

Delivery implant 10 can be manufactured by standard manufacturing techniques. In one process wall 12 is injection molded or extruded into the desired shape. The wall section is filled in different procedures, such as first filling the compartment with the pharmaceutically acceptable beneficial agent composition, the interface layer 21 and the expandable composition 19, or the compartment is filled with the expandable driving member 19, the layered partition 21 next is added thereto in layered arrangement, then the compartment is filled with the pharmaceutically acceptable beneficial agent composition. Optionally, the interface partition 21 may be added first, followed by adding either the pharmaceutically acceptable formulation and the expandable push member on either side thereof. Then, the ends are sealed with an end cap. At least one passageway is drilled in the lead end of the manufactured assembly. Optionally, a passageway is drilled, or preformed in the wall, or a passageway is sealed with a break-off tab that is broken open, or cut open, or the like, at the time of use to connect through the passageway the beneficial agent composition with the exterior of delivery implant 10.

DISCLOSURE OF EXAMPLES OF THE INVENTION

The following examples are merely illustrative of the present invention and they should not be construed as limiting the scope of the invention in any way, as these examples and other equivalents thereof will become more apparent to those skilled in the art in the light of the present disclosure, the drawings and the accompanying claims.

EXAMPLE 1

A composition for forming a wall is prepared from the following materials: 59.5% cellulose acetate butyrate, 25.5% polymethylmethacrylate and 15% tributyl citrate is extruded as a tube of the following dimensions: a length of 2.48 cm, an outside diameter of 0.341 cm, an inside diameter of 0.290 cm, and a wall thickness of 10 mils (0.254 mm).

Next, a expandable push composition is prepared by blending 66.33% sodium carboxy vinyl polymer, 28.71% of sodium chloride, 3.96% of polyvinylpyrrolidone and 1% of magnesium stearate into a homogeneous blend. The blend is pressed into a tablet at a compression force of 5 lbs. to produce a round tablet 0.190 inches (4.82 mm) high, 0.110 inches (2.79 mm) in diameter, and weighing 47 mg.

An interface layer is prepared from microcrystalline wax by cutting layer comprising a height of 0.096 cm (0.038 inches) and a 0.290 cm (0.114 inches) diameter.

A pharmaceutically acceptable vehicle is prepared by blending 62.61% of sesame oil, 9.39% ethylene vinyl acetate copolymer comprising a 40% acetyl content, and 28% of micronized norgestomet.

An end cap for closing the tubular housing is prepared by pressing cellulose acetate butyrate into an end cap of 0.5 mil (0.02 mm) thick, and separately pressing the cellulose acetate butyrate into a lead cap 0.22 cm thick and weighing 3.6 mg each.

Next, the dispenser is assembled by first inserting the expandable push composition into one end of the tubular housing followed by inserting the end cap into the tubular housing to form the closed rear end. Then, the wax interface layer is inserted into the opened lead end, distant from the closed rear end, and the wax layer positioned in laminated arrangement with the expandable, push tablet. Then, the pharmaceutically acceptable vehicle comprising the norgestomet is charged through the opened lead end into the lumen to fill the lumen from the wax layer to the opened end. The opened lead end is sealed with the lead cap and an exit port 0.127 cm (50 mil) is drilled through the lead cap to produce the implantable dispenser.

EXAMPLE 2

The procedure of Example 1 is followed in this example to produce implant dispenser 10. In this example, the exterior surface of the dispenser is spray coated with a composition comprising 54 wt% cellulose acetate butyrate, 36 wt % polymethylmethacrylate and 10 wt % tributyl citrate. The exterior coat is 13.3 mils (0.52 mm) thick and after drying weighed 115 mg. A 50 mil (1.97 mm) exit port was drilled through the coated membrane and the wall of the implant dispenser. The implant delivers a beneficial agent for 180 days.

EXAMPLE 3

An implant dispenser is manufactured by following the procedures of Examples 1 and 2. In this example, the wall of the dispenser comprises 56 wt % cellulose acetate butyrate, 24 wt % polymethyl methacrylate, and 20 wt % tributyl citrate; the expandable push composition comprises 66.33 wt % sodium carboxyvinyl polymer, 8.71 wt % sodium chloride, 3.96 wt % polyvinyl pyrrolidone and 1 wt % magnesium stearate; the pharmaceutically acceptable formulation comprises 54 wt % sesame oil, 28 wt % norgestomet and 18 wt % ethylene vinyl acetate copolymer comprising a 40% vinyl acetate content; and an interface layer position between the pharmaceutically acceptable formulation and the expandable layer comprising 100 wt % microcrystalline wax. The implant comprises a length of 2.54 cm, a wall thickness of 0.025 cm, an outside diameter of 0.318 cm and an inside diameter of 0.267 cm. The expandable push layer weighed 45.1 mg, and is made as a round tablet 0.470 cm in height and 0.274 cm in diameter. The pharmaceutically acceptable formulation weighed 114.4 mg. The device comprises a 0.127 cm exit port.

EXAMPLE 4

The implant dispenser of Example 3 is made in this example, with all procedures as set forth, except that in this example the pharmaceutically acceptable formulation comprises 44.6 wt % sesame oil, 28 wt % norgestomet, 20.2 wt % ethylene vinyl acetate copolymer comprising 40% acetyl content, and 7.2 wt % isopropyl myristate. The pharmaceutically acceptable formulation weighed 115.3 mg.

EXAMPLE 5

The implant dispenser of Example 3 is made in this example, with all procedures as set forth, except that in this example the pharmaceutically acceptable formulation comprises 60 wt % microcrystalline wax, 28 wt % norgestomet, and 12 wt % microcrystalline cellulose. The implant dispenser comprises a rear end seal comprising 100 wt % polycarbonate and a lead end seal comprising 100 wt % polycarbonate with an exit port. The implant dispenser optionally sprayed coated with a membrane composition comprising 54 wt % cellulose acetate butyrate, 36 wt % polymethylmethacrylate and 10 wt % tributyl citrate. The interface layer positioned between the pharmaceutically acceptable formulation and the expandable push layer comprises 100 wt % wax.

EXAMPLE 6

An implant dispenser for delivering a beneficial agent to livestock is prepared according to this example. First, an expandable push composition shaped like a tablet is prepared according to the accompanying procedure. Using a 12 mesh screen, size 6,466 grams of sodium chloride for use in the granulation. Next, weigh out 13 kilograms of Sodium Carbomer ®, a carboxyvinyl polymer, 5.627 kilograms of the sodium chloride sized above and 0.776 kilograms of Povidone ®, USP, a polyvinylpyrrolidone, into a clean mixing vessel. Mix the three ingredients in a Hobart ® mixer for four minutes at speed setting one. Into a separate vessel, weigh the following ingredients: 7 liters of ethanol (95% USP) and 370 liters of purified water. The solution of ethanol/water is slowly added to the powder mixture above, and mixed for 14 minutes on speed setting 2 to achieve an even consistency. This wet granulation is passed through a 1 mesh stainless steel screen using a conventional granulator machine. The granules are then spread to a depth of approximately ½ inch on paper lined oven trays and dried at 50° C. for 15 hours. The dried granules are then passed through a 12 mesh stainless screen. The resultant material weighs 20,400 grams. Next, 206 grams of lubricant are passed through a 40 mesh screen and added to the dried granulation above and mixed for 2 minutes at slow speed. Moisture content of the completed granulation of 20,302 grams is 6.8%. Tablets of the above formulation are compressed on a laboratory scale Carver ® press using 0.107" round, flat faced tooling. Approximately 45 mg of granulation is placed into the die cavity and compressed to produce tablets with heights of 0.185 inch (average) and weights of 0.045+/−0.002 grams.

Next, a wall housing member is prepared according to the accompanying procedure. First, using a Brabender 50 cc bowl mixer heated to 150° C., add 12 grams of polymethyl methacrylate, (PMMA), and mix at 40 RPM to fuse the material. Then, 5 grams of tributyl citrate is added to soften the polymethyl methacrylate (PMMA). While the PMMA is softening, lower the temperature to 110° C. In another mixing vessel, add 5 grams of tributyl citrate to 28 grams of cellulose acetate butyrate, and mix using a spatula; then add this mixture to the mixture in the Brabender bowl. The temperature in the Brabender mixer is then raised to 180–190° C. to complete the melt of the cellulose acetate butyrate. The temperature is maintained for five minutes at the higher temperature, then over the course of 20 minutes, lower the temperature back to 110° C. The material is then removed from the bowl and prepared for feeding to the extruder by chopping it into small pieces. Then feed the above material into a ¾" Brabender extruder equipped with an extrusion die with the following dimensions: Die O.D.: 0.160"; Mandrel O.D.: 0.140". Tubing is fabricated under the following extrusion conditions: Barrel Temperature setting: 210° F.; Die Temperature setting: 225° F., Rod: 135°-150° C.; Pressure (PSI): 2000 PSI; Take-up speed: 1.6 ft/min.; and, Screw RPM: 4.

The pharmaceutically acceptable vehicle/carrier is a mixture of ethylene vinyl acetate copolymer (40% vinyl acetate content) and sesame oil. Weigh out 6.0015 grams of said copolymer and add to 40 ml of sesame oil in a 100 ml beaker. Cover the beaker with aluminum foil and place in a water bath which has been situated on a heat/stir plate. The water bath is maintained at 80° C., and the stir mechanism turned on. A stir rod is added to the beaker to ensure adequate mixing of components. The mixture is heated and mixed under these conditions for approximately 6 to 7 hours. The mixture is then homogenized with a Polytron ® tissue homogenizer (high shear mixer) for 3 minutes then allowed to cool to room temperature.

A drug is added to the pharmaceutically acceptable vehicle/carrier by weighing 10.8 grams of previously prepared ethylene vinyl acetate copolymer gel into a tared 30 ml beaker. Add 4.2 grams of Norgestomet (micronized drug) a little at a time to the gel, stirring with a spatula until all drug powder is homogeneously mixed in. The drug gel is allowed to set for approximately one hour prior to filling subassemblies.

Then, the implant dispenser is assembled according to the accompanying disclosure. The tubing housing member as prepared above is cut to 1 inch lengths with a razor blade. Tablets produced above are inserted int the bottom of the tubing such that the bottom of the tablet is flush with the bottom of the cut tube. Next, a wax interface is put in place in the following manner: Fill a syringe with melted wax and melt wax set up for several minutes or until it is molten. Pump warm wax out of the syringe without a needle. The noodle of wax which results from this is just wide enough in diameter to fit neatly into tube from the top without getting wax on the insides of the tube. A length of the extruded noodle which weighs approximately 0.002 grams is cut using a razor blade. This piece of wax is then packed down on top of the osmotic tablet where it adheres to the walls of the tube thereby preventing material transfer between drug reservoir gel and osmotic expandable push engine.

The end of the tube housing the expandable push engine is then "dip coated" in a solution of cellulose acetate butyrate in methylene chloride. The coating is allowed to dry overnight. A coating of approximately 0.005 inches (5 mils) is applied. This dip coating is done to ensure no leakage from the system and also to ensure good contact of coating material over entire system.

The dried subassemblies are filled with the drug gel from above. A 2 cc syringe and an 18 gauge needle with a flat end are used for filling. The drug gel is back filled into the syringe and de-aerated to release air bubbles. The needle is attached and systems are filled from the bottom (from the wax interface) up taking care that the needle end remains submerged in the gel so as to prevent air bubbles from forming in the tube. Fill weights are approximately 127 mg weight (with drug loading at 28% of that weight). Systems are allowed to set for 1 hour prior to capping.

Dip Capping of the open end of the housing ensures a closed system prior to spray coating. A paste of cellulose acetate butyrate is prepared using methylene chloride as the solvent. The open end of the subassembly is dipped in the paste to seal the top of the system. The housing is allowed to dry for at least for 24 hours prior to spray coating.

Coating solution is prepared as follows: Measure 3472 ml of methylene chloride into a mixing vessel and place in a hood equipped with a solution mixer. Slowly add 59.5 grams of polymethyl methacrylate to the methylene chloride while mixing continuously. Continue mixing for 1½ hours. Then, slowly add 89.25 grams of cellulose acetate butyrate, and 16.53 grams of tributyl citrate (plasticizer). Mix for approximately ½ hour. Next add 305 ml methanol and mix for an additional 1 hour.

The exterior coating is done using an Aeromatic ® coater equipped with a Zenith pump, operating at a pump speed of 22 ml/minutes, with an atomizing air pressure of 1.8-2.4 bars, an inlet drying temperature of 39° C., an outlet temperature of 19° C. and a charge of 110 housings means 100 implants were placed in the coater. An exit port is formed, by using a 50 mil (1.27 mm) drill bit, an orifice is drilled at the top of the system (the top of the system is the end with the drug fill) until the cap and spray coat are penetrated. The implants are now ready for use.

DISCLOSURE OF USING THE INVENTION

An embodiment of the invention pertains to a method for delivering a beneficial agent such as a drug to an animal. The method comprises implanting a delivery system, shaped, sized and adapted as an implant into an animal, such as into a muscle thereof. The method comprises the steps of: (A) admitting into an animal a delivery system comprising: (1) a housing comprising an internal lumen, which lumen comprises: (2) a pharmaceutically acceptable drug formulation; (3) an expandable push composite; (4) an interface layer fluid interposed between the pharmaceutically acceptable drug formulation and the expandable composition; and (5) at least one orifice in the device communicating with the lumen; (B) imbibing fluid through the wall for causing the expandable means to expand and push against the beneficial agent formulation; and (C) delivering the beneficial agent formulation from the delivery implant by the expandable means continuously expanding at a controlled rate thereby causing the beneficial agent formulation to be delivered in an effective amount through the orifice to the animal over a prolonged period of time.

The novel devices of this invention use means for the obtainment of precise release rates in the environment of use while simultaneously maintaining the integrity of the device. While there has been described and pointed out features of the invention as applied to presently preferred embodiments, those skilled in the art will appreciate that various modifications, changes, additions and omissions in the devices illustrated and described can be made without departing from the spirit of the invention.

We claim:

1. An improvement in an implantable dispenser for delivering a beneficial agent to an animal, the implantable dispenser comprising:
   (a) a wall in at least a part comprising a composition permeable to the passage of fluid, which wall surrounds;
   (b) an internal lumen;

(c) a composition when contacted by fluid increases in volume for displacing a formulation from the implantable dispenser; and, (d) an exit port in the wall that connects the exterior of the implantable dispenser with the lumen, and wherein the improvement comprises:

(e) a pharmaceutically acceptable beneficial agent formulation in the lumen, which formulation comprises (1) a beneficial agent; (2) an oil that is a carrier for the agent; and (3) a polymer that imparts gel properties to the oil, whereby, through the combined operations of (a), (c), (d) and (e) the beneficial agent formulation is delivered at a rate controlled by the implantable dispenser to the animal over time.

2. The improvement in an implantable dispenser for delivering a beneficial agent according to claim 1, wherein the polymer that imparts gelation comprises a member selected from the group consisting of olefin, condensation and addition polymers.

3. The improvement in an implantable dispenser for delivering a beneficial agent according to claim 1, wherein the polymer that comprises gelation comprises a member selected from the group consisting of ethylene-vinyl ester copolymer comprising a vinyl acetate content of 4% to 80%.

4. The improvement in an implantable dispenser for delivering a beneficial agent according to claim 1, wherein the beneficial agent is a member selected from the group consisting of dromostanolone, dromostanolone propionate, chlormadinone, chlormadinone acetate, melengestrol acetate, norgestomet, dimethisterone, ethisterone, hydroxyprogesterone, estradiol, 17α-acetoxy-11β-methyl-19-norpregn-4-ene-3,20-dione, 3(3-oxo-11β,13β-dialkyl-17β-hydroxygon-4-en-17α-yl) propionic acid-lactone, 3(3-oxo-11βmethyl-17β2-hydroxyestr-4-en-17α-yl) propionic acid lactone, 11,13β-dialkyl-17-lower alkyl-gon-4-en-3-one, and 19-nor-pregn-4-ene-3,20-dione.

5. The implantable dispenser for delivering the beneficial agent to an animal according to claim 1, wherein the beneficial agent comprises a member selected from the group consisting of oxytocin, vasopressin, adrenocorticotropic, prolactin, luliberin, luteinizing hormone, insulin, somatostatin, glucagon, interferon, gastrin, tetragastrin, pentagastrin, urogastrone, secretin, calcitonin, endorphin, angiotensin, renin, bradykinin, bacitracin, polymyxin, colistin, tyrocidine and gramicidins.

6. The implantable dispenser for delivering the beneficial agent to an animal according to claim 1, wherein the beneficial agent is a member selected from the group consisting of monoclonal antibody, vaccine, somatotropin, cosyntropin, gonadotropin, thyrotropin releasing hormone, thyroid stimulating hormone, and pancreozymin.

7. The implantable dispenser for delivering a beneficial agent to an animal according to claim 1, wherein a coat is on the exterior surface of the wall, said coat a means for governing the volume of external fluid that enters the implantable dispenser.

8. An implantable dispenser for delivering a beneficial agent to an animal, the implantable dispenser comprising:

(a) a wall in at least a part comprising a semipermeable composition;
(b) an internal lumen;
(c) a composition that increases in volume when contacted by fluid in the lumen and thereby aids in pushing a beneficial agent formulation from the implantable dispenser; and,
(d) an exit port in the wall that connects the exterior of the implantable dispenser with the lumen, the implantable dispenser characterized by:
(e) a pharmaceutically acceptable formulation in the lumen, the formulation comprising (1) a beneficial agent for delivering to an animal; (2) a nontoxic oil carrier for the beneficial agent; (3) a nontoxic co-solvent for increasing the amount of beneficial agent present in the oil carrier; and (4) a nontoxic polymer gellant for the oil, whereby, through the operations of (a), (c), (d) and (e) the beneficial agent is delivered at a rate controlled by the implantable dispenser to the animal over time.

9. The implantable dispenser for delivering a beneficial agent to an animal according to claim 8, wherein a composition comprising means for maintaining the integrity of both the composition that increases in volume and the pharmaceutically acceptable formulation is positioned therebetween.

10. The implantable dispenser for delivering a beneficial agent to an animal according to claim 8, wherein the composition that increases in volume comprises a hydrogel.

11. The implantable dispenser for delivering a beneficial agent to an animal according to claim 8, wherein the composition that increases in volume comprises an osmagent.

12. The implant dispenser for delivering a beneficial agent to an animal according to claim 8, wherein a coat is on the exterior surface of the wall, said coat a means for governing the volume of external fluid that enters the implantable dispenser.

13. The implantable dispenser for delivering the beneficial agent to an animal according to claim 8, wherein the beneficial agent comprises a member selected from the group consisting of oxytocin, vasopressin, adrenocorticotropic, prolactin, luliberin, luteinizing hormone, insulin, somatostatin, glucagon, interferon, gastrin, tetragastrin, pentagastrin, urogastrone, secretin, calcitonin, enkephalin, endorphin, angiotensin, renin, bradykinin, bacitracin, polymyxin, colistin, tyrocidin and gramicidins.

14. The implantable dispenser for delivering the beneficial agent to an animal according to claim 8, wherein the beneficial agent is a member selected from the group consisting of monoclonal antibody, vaccine, somatotropin, cosyntropin, gonadotropin, thyrotropin releasing hormone, thyroid stimulating hormone, and pancreozymin.

15. The implantable dispenser for delivering the beneficial agent to an animal according to claim 8, wherein the exit port is formed by fluid removing a port forming composition from the dispenser.

16. The implantable dispenser for delivering the beneficial agent to an animal according to claim 8, wherein the implantable dispenser comprises more than one exit port.

17. The implantable dispenser for delivering the beneficial agent to an animal according to claim 8, wherein the polymer gellant comprises a member selected from the group consisting of ethylenevinyl formate copolymer, ethylene-vinyl acetate copolymer, ethylenevinyl hexanoate copolymer, ethylene-vinyl propionate copolymer, ethylene-vinyl pentanoate copolymer, ethylene-vinyl isopropylate copolymer, ethylene-vinyl diacetate copolymer, ethylene-vinyl tertbutylacetate copolymer, ethylene-vinyl phenylacetate copolymer and ethylene-vinyl benzoate copolymer.

18. The implantable dispenser for delivering the beneficial agent to an animal according to claim 8, wherein the cosolvent comprises a member selected from the group consisting of butyl stearate, stearyl stearate, propyl stearate, isopropyl stearate, 2-ethylhexyl stearate, myristyl stearate, decyl stearate, benzyl stearate, butyl palmitate, cetyl palmitate, 2-ethylhexyl palmitate, isopropyl palmitate, butyl alurate, isopropyl laurate hexyl laurate, cetyl laurate, isopropyl myristate, butyl myristate, myristyl myristate, lauryl myristate, isoamyl myristate, decyl oleate, di-isopropyl adipate, di-2-ethylhexyl adipate, di-n-butyl sebacate, di-2-ethylhexyl sebacate, di-isopropyl sebacate, isopropyl linoleate, cetyl lactate, lauryl lactate, myristyl lactate, decyl oleate, and isodecyl oleate.

19. The implantable dispenser for delivering the beneficial agent to an animal according to claim 8, wherein the polymer gellant comprises a member selected from the group consisting of olefin polymers, condensation polymers, addition polymers, cellulosic polymers, saccharide polymers, and organo-silicon polymers.

* * * * *

UNITED STATES PATENT AND TRADEMARK OFFICE
CERTIFICATE OF CORRECTION

PATENT NO. : 5,112,614

DATED : May 12, 1992

INVENTOR(S) : Judy A. Magruder, James B. Eckenhoff, Jeremy C. Wright

It is certified that error appears in the above-identified patent and that said Letters Patent is hereby corrected as shown below:

Column 17, line 36, "1762" should read --17β--;
Column 19, line 10, "alurate" should read --laurate--.

--laurate--.

Signed and Sealed this

Sixth Day of September, 1994

Attest:

BRUCE LEHMAN

*Attesting Officer*    *Commissioner of Patents and Trademarks*